United States Patent
Feiglin

(10) Patent No.: US 9,108,193 B2
(45) Date of Patent: Aug. 18, 2015

(54) COLLECTION/EXTRACTION CONTAINER FOR BIOLOGICAL MATERIAL IN FORENSIC SAMPLES

(75) Inventor: Marc N. Feiglin, East Brunswick, NJ (US)

(73) Assignee: TECAN TRADING AG, Mannedorf (CH)

( * ) Notice: Subject to any disclaimer, the term of this patent is extended or adjusted under 35 U.S.C. 154(b) by 561 days.

(21) Appl. No.: 12/669,922

(22) PCT Filed: Jul. 23, 2007

(86) PCT No.: PCT/EP2007/057561
§ 371 (c)(1),
(2), (4) Date: Jun. 7, 2010

(87) PCT Pub. No.: WO2009/012808
PCT Pub. Date: Jan. 29, 2009

(65) Prior Publication Data
US 2010/0248213 A1 Sep. 30, 2010

(51) Int. Cl.
*B01L 3/00* (2006.01)
*G01N 1/40* (2006.01)

(52) U.S. Cl.
CPC ............ *B01L 3/5021* (2013.01); *G01N 1/4044* (2013.01); *B01L 3/5029* (2013.01);
(Continued)

(58) Field of Classification Search
CPC ..... B01L 3/502; B01L 3/5021; B01L 3/5453; B01L 2300/0681; B01L 9/06
See application file for complete search history.

(56) References Cited

U.S. PATENT DOCUMENTS 4,439,319 A 3/1984 Rock
5,164,575 A * 11/1992 Neeley et al. ............ 235/472.01
(Continued)

FOREIGN PATENT DOCUMENTS

WO WO 2005021130 A1 * 3/2005 ............ B01D 25/21
WO WO 2006010584 A1 * 2/2006

OTHER PUBLICATIONS

Written Opinion of the International Searching Authority of International Application No. PCT/EP2007/057561.

*Primary Examiner* — Lyle Alexander
*Assistant Examiner* — Matthew Krcha
(74) *Attorney, Agent, or Firm* — Notaro, Michalos & Zaccaria P.C.

(57) ABSTRACT

Relates to a collection/extraction container (1) for collecting solid forensic samples (2) and/or for extracting biological material from these solid forensic samples (2) and its use. The container (1) has a top opening (3) for the insertion of a solid forensic sample (2). The container (1) comprises a basket (7) and an essentially horizontal intermediate floor (8) for the retention of the solid forensic sample (2) during digestion/lysis and extraction, the intermediate floor (8) being permeable to fluids and dividing the inner chamber (5) into an upper sample space (9) and a lower fluid space (10). The container according to the invention is characterized in that is comprises an essentially vertical channel (11), which is accomplished to allow a pipetting needle (12) to be inserted through the sample space (9) and into the fluid space (10) in that the channel (11) has a top orifice (13) that is situated nearby a top opening (3) of the container (1) and in that the channel (11) penetrates the intermediate floor (8) in a bottom orifice (14), wherein the container (1) also comprises a partition wall (15) that at least partially surrounds the channel (11) and that separates the latter from the upper sample space (9).

16 Claims, 1 Drawing Sheet

(52) U.S. Cl.
CPC .......... *B01L3/50255* (2013.01); *B01L 3/50851* (2013.01); *B01L 3/50853* (2013.01); *B01L 3/50855* (2013.01); *B01L 3/545* (2013.01); *B01L 2200/027* (2013.01); *B01L 2300/022* (2013.01); *B01L 2300/046* (2013.01); *B01L 2300/0618* (2013.01); *B01L 2300/0829* (2013.01); *Y10T 436/25* (2015.01)

(56) References Cited

U.S. PATENT DOCUMENTS

| | | | |
|---|---|---|---|
| 5,888,831 A | | 3/1999 | Gautsch |
| 5,962,247 A | * | 10/1999 | Foote et al. ............... 435/21 |
| 6,506,167 B1 | * | 1/2003 | Ishimito et al. ............ 600/577 |
| 6,827,907 B2 | * | 12/2004 | Fattinger et al. ........... 422/562 |

* cited by examiner

COLLECTION/EXTRACTION CONTAINER FOR BIOLOGICAL MATERIAL IN FORENSIC SAMPLES

The present invention relates to a collection/extraction container for collecting solid forensic samples and/or for extracting biological material from these forensic samples. This container has a top opening for the insertion of a forensic sample. The top opening is surrounded by an essentially vertical wall, which encloses an inner chamber that is limited in depth by a bottom. The wall and the bottom of the container are impermeable to fluids. The container also comprises a basket and an essentially horizontal intermediate floor for the retention of the solid forensic sample during washing, i.e., digestion/lysis and extraction. The intermediate floor is permeable to fluids and divides the inner chamber into an upper sample space and a lower fluid space.

The collection of samples containing nucleic acid in order to determine the genetic code is currently increasingly gaining in significance. In connection with combating crime, the collection of genetic samples in the meaning of a "genetic fingerprint" is becoming more and more important in two regards: firstly, the genetic code is to be acquired from criminals who have already been arrested and secondly the acquired data is to be compared to unknown traces found at a crime scene, for example. In the first case, fresh and clearly identified samples are used to build up a data bank, which may be accessed in the second case. However in the second case, the collected samples are often incomplete, contaminated, and damaged, thus complicating the forensic work. Additionally, individual countries have already begun to collect biological samples in order to preventively acquire the genetic code of all individuals entering the country or even all the inhabitants of the country.

The attribute "forensic" refers to anything, which has a legal or criminological character. The term is thus not only restricted to the fields of criminal law (e.g., legal medicine), but rather comprises any professional activity within any legal proceeding. Forensically relevant samples also comprise proteins (e.g., the prions causing Creutzfeld-Jacob syndrome, or bovine spongiform encephalopathy, or BSE respectively), viruses, bacteria, and other microorganisms, human or animal bodily fluids (such as blood, sputum, feces, sperm, and urine), and single cells (such as oral mucosa cells and hair follicles).

Methods for isolating and analyzing human deoxyribonucleic acid (DNA) ribonucleic acids (RNA) are known from the prior art (cf., for example, Molecular Diagnostics: Isolation and Analysis of Human Genomic DNA, 1998 Promega Notes No. 68, p. 20). These methods comprise the PCR methods (PCR=Polymerase Chain Reaction) well known per se for increasing the sample yield and thus the sensitivity of the analysis.

Containers for collecting samples and for manually preparing the collected samples for an analysis or a PCR reaction are known from WO 2004/105949 A1. Containers for performing the collection and subsequent PCR reaction in the field are known from US 2004/0214200 A1. However, these known methods appear quite complicated and the containers appear unsuitable for automated and/or robotic processing of samples.

Automated nucleic acid isolation is e.g., known from U.S. Pat. No. 5,863,801. However, the device described in this patent is designed to be used as a stand-alone device and does not work with the existing automation and instruments typically used in forensics and research laboratories, such as a TECAN automated liquid handler (TECAN Schweiz A G, Seestrasse 103, CH-8708 Mannedorf, Switzerland). Given the resources required for such a laboratory to validate their processes, it is of significant value to have a consumable that can closely mimic their validated manual processes and be used on existing instrumentation.

A device for incubation, centrifugation and separation of DNA samples on a solid support is known as the Slicprep™ 96 device from PROM EGA Corp. (2800 Woods Hollow Road, Madison, Wis. 53711 USA). This device is made from polypropylene and is based on a 96-deep well microplate, a 96 spin basket unit, and a collar for raising the baskets. In the incubation mode, the solid supports or forensic samples (e.g. dried buccal swabs) are placed in the baskets that are fully inserted in the deep well plate. Digestion buffer or lysis buffer is added to cover the samples and the sealed unit is incubated at a desired temperature. The baskets are then raised and a collar is inserted so that centrifugation in a swinging plate rotor will remove the extract, i.e., the DNA-containing solution from the solid supports or forensic samples. After removal of the 96-spin basket unit and the collar, the deep well plate can then be placed on a workstation for purifying the DNA. Although this device has been designed to make DNA extraction from forensic samples more automation compatible, manual procedure steps are still required for adding the collar and then later removing the collar and the basket unit.

Nucleic acid isolation that is carried out similarly as just described and that also requires significant manual steps during the process is known from FITZCO Inc. (4300 Shoreline Drive, Spring Park, Minn. 55384, USA). The FITZCO Spineze™ device is a single tube device consisting of a basket unit and an Eppendorf type receiving tube. In the initial extractions steps, solid supports containing DNA (i.e., swabs) are placed in the basket, which is then inserted into the Eppendorf type tube. Digestion or lysis buffers are added to cover the forensic samples and the sealed unit is incubated and later centrifuged to make the DNA-containing solution flow from the basket to the tube. The basket is then manually removed and the tube can be placed on a workstation for purifying the DNA.

Another system that is known from TECAN consists of two tubes, which can be attached end-to-end with a "filter", placed between them for processing. A sample tube contains the swab or other DNA containing forensic material. Buffers are added to the sample tube for initial processing and a receiving tube is attached upside down to the top of the sample tube. A rack with an array of such "doubletubes" is moved into a "flipping" device, which rotates the two connected tubes so that the liquid can flow via the filter from the now upper sample tube into the lower receiving tube during a subsequent centrifugation. The tubes then may be separated. Also this system needs manual manipulation and in addition, special devices for flipping the tubes are required.

An object of the present invention is to suggest an alternative device and/or an alternative method, which enable bound molecules, such as nucleic acids, to be processed and removed fully automatically from solid supports, such as buccal swabs.

This object is achieved according to a first aspect by a collection/extraction container for collecting solid forensic samples and/or for extracting biological material from these forensic samples according to the features of claim 1. The container has a top opening for the insertion of a forensic sample. The top opening is surrounded by an essentially vertical wall, which encloses an inner chamber that is limited in depth by a bottom. The wall and the bottom are impermeable to fluids. The container comprises a basket and an essentially horizontal intermediate floor for the retention of the solid forensic sample during washing, i.e., digestion/lysis and extraction, the intermediate floor being permeable to fluids and dividing the inner chamber into an upper sample space and a lower fluid space.

The container according to the present invention is characterized in that it comprises an essentially vertical channel, which is accomplished to allow a pipetting needle to be inserted through the sample space and into the fluid space in that the channel has a top orifice that is situated nearby the top opening of the container and in that the channel penetrates the intermediate floor in a bottom orifice, wherein the container also comprises a partition wall that at least partially surrounds the channel and that separates the latter from the upper sample space.

This object is achieved according to a second aspect, in that a method for extracting biological material from forensic samples is suggested. The method according to the present invention comprises the following method steps:

(a) Providing at least one container 1 with an accessible top opening 3, an upper sample space 9 with a basket 7, a fluid space 10, and a channel 11;

(b) Placing solid forensic samples 2 through the top opening 3 into the basket 7 in the upper sample space 9 of the at least one container 1;

(c) Adding digestion/lysis buffer into the basket 7 so that both the lower fluid space 10 of the container 1 is filled and the upper sample space 9 is also filled enough to cover the forensic sample 2;

(d) Sealing the entire device 1 and then allowing to incubate to enable the extraction process to occur;

(e) Unsealing or opening the device 1 after incubation and removing a volume of digestion buffer by accessing the bottom of the lower fluid space 10 through the essentially vertical channel 11;

(f) Placing the device 1 in a centrifuge and spinning so that any remaining buffer in the solid forensic sample 2 collects down in the bottom of the inner chamber 5;

(g) Removing the remaining volume of digestion buffer that has collected at the bottom of the lower fluid space 10 by the centrifugation by access through the essentially vertical channel 11, wherein the solid forensic samples 2 are retained in the basket 7 in the sample space 9 of the at least one container 1 during all the steps (c) through (g).

The volume removed preferably is combined with the volume removed earlier. This combined sample is now ready for purification of nucleic acids using commercial kits.

Additional preferred features according to the present invention result from the dependent claims.

Advantages of the present invention comprise:

The same container that is used for extraction of biological material from e.g., the surfaces of solid forensic samples can also be used for the collection of said forensic samples in the field.

The container provides a port or channel that enables access to the bottom of the container for a pipette tip without requiring removal of the basket that contains the solid forensic sample.

The container can be racked into an array of e.g., 6×8 tubes and utilized fully automated, as there is no need to assemble or disassemble parts during processing. Thus, common automation devices such as centrifuges, robotic arms, PCR thermostatic tables etc. can be used.

There is no need for special devices for flipping the tubes or racks that contain the tubes.

Labeling the container with an identification tag provides clear identification of a particular forensic sample and the biological material extracted from this solid forensic sample.

The present invention will be explained in greater detail on the basis of exemplary embodiments and schematic drawings, which do not restrict the scope of the present invention. Whereas it is shown in:

FIG. 1 vertical partial sections through two different racks having four different embodiments of the container according to the present invention:

Figure 2A:
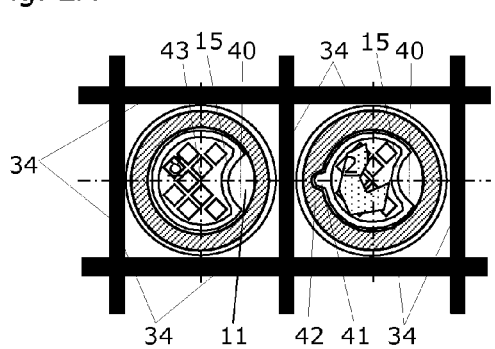
Figure 2B:
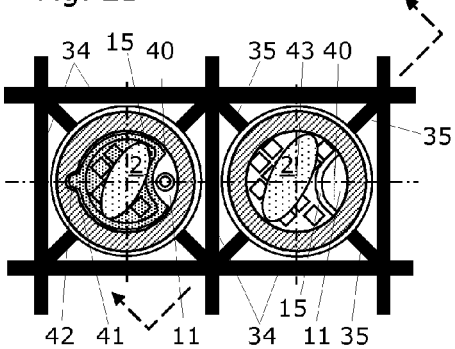
Figure 3:
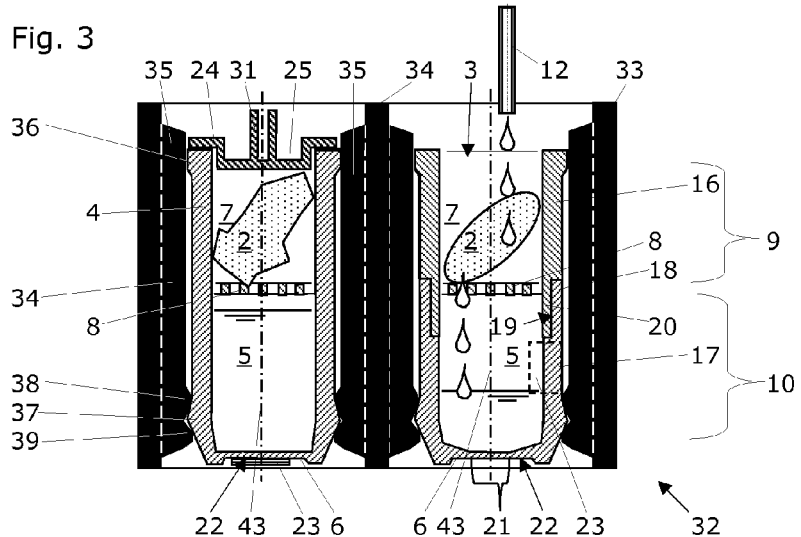

FIG. 2 horizontal partial sections through the two racks of FIG. 1:

FIG. 2A shows a collecting rack with friction fit inserted containers;

FIG. 2B shows an extracting rack with containers held in place by retention means;

FIG. 3 vertical partial sections through a rack having two different embodiments of the container according to the present invention.

Figure 1A:
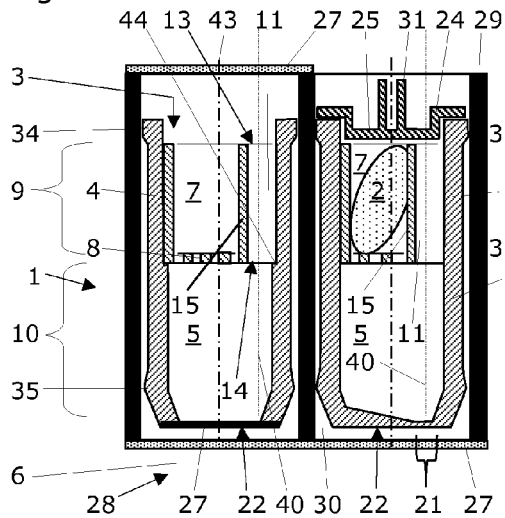
FIG. 1A shows flat bottom containers with friction fit inserted baskets.

FIG. 1 shows vertical partial sections through two different racks having four different embodiments of the container 1 according to the present invention. FIG. 1A exhibits flat bottom containers with friction fit inserted baskets. Both containers shown are collection/extraction containers 1 for collecting solid forensic samples 2 and/or for extracting biological material from these forensic samples 2. Solid forensic samples 2 are typically selected from a group, which comprises a gauze pad or buccal swab; a finding; a filter paper or WHATMAN FTA paper (Whatman plc., 27 Great West Road, Brentford, Middlesex, TW8 9BW, UK) respectively; a solid, sheet-like material for adsorbing nucleic acids or other biological molecules, such as preparation gels and cellulose membranes; and a textile piece. In most of the cases the biological material sample to be extracted is selected from a group comprising bodily fluids, cells, DNA, RNA, proteins, microorganisms, and viruses. It is especially preferred however, to collect nucleic acid material such as DNA and/or RNA with a buccal swab and to extract the nucleic acid material from this buccal swab within the container 1 of the invention.

Each container 1 has a top opening 3 for the insertion of a solid forensic sample 2, the top opening 3 being surrounded by an essentially vertical wall 4, which encloses an inner chamber 5 that is limited in depth by a bottom 6. The wall 4 and the bottom 6 are impermeable to fluids. Each container 1 comprises a basket 7 and an essentially horizontal intermediate floor 8 for the retention of the solid forensic sample 2 during washing, i.e., digestion/lysis and extraction. The intermediate floor 8 is permeable to fluids and divides the inner chamber 5 into an upper sample space 9 and a lower fluid space 10.

"Fluids" in the context of the present invention are to be understood as liquids, gases, or liquid/gas mixtures. "Solid" is interpreted as hard or soft material other than fluidic. A "sample" preferably is a solid forensic sample, but it can be any other sample that contains biological material. A "finding" can be an artifact or casework sample as found at a criminal scene or any other non-specific solid material that contains biological material that can be extracted.

The container 1 according to the invention comprises an essentially vertical channel 11, which is accomplished to allow a pipetting needle 12 to be inserted through the sample space 9 and into the fluid space 10. This is accomplished in that the channel 11 has a top orifice 13 that is situated nearby the top opening 3 of the container 1 and in that the channel 11 penetrates the intermediate floor 8 in a bottom orifice 14. The container 1 also comprises a partition wall 15 that at least partially surrounds the channel 11 and that separates the latter from the upper sample space 9.

Preferably, the wall 4 of the container 1 is essentially cylindrical at least in the region of the upper sample space 9. It is also preferred that the channel 11 is arranged off-center and partially formed by the wall 4 and the partition wall 15 in order to leave as much space as possible for a solid forensic sample 2 that can be introduced into the upper sample space 9 and that can be kept here by the basket 7. It is especially preferred that the basket 7 of the container 1 is sized to accommodate a buccal swab.

As the channel 11 preferably is arranged off-center, it defines an essentially vertical off-center axis 40. The bottom 6 and/or the lower section 17 of the wall 4 thus are preferably accomplished to form a fluid collecting area 21, which is at a lower level then the rest of the bottom 6 of the container 1, the fluid collecting area 21 lying on this essentially vertical off-center axis 40.

Figure 1B:
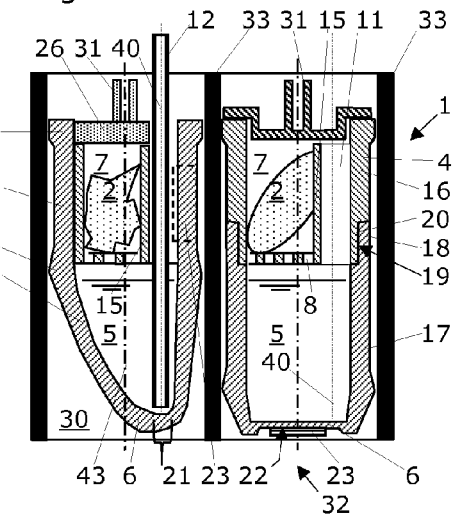
FIG. 1B shows a container shaped as a PCR tube and a container consisting from two parts.

As shown in FIG. 1A, the basket 7 may be accomplished as a single injection molded piece of polymer material that is inserted into the inner chamber 5 of the container 1. Alternately as shown in FIG. 1B (see there on the right side), the basket 7 is accomplished as a part of an upper section 16 of the wall 4 and formed together with this upper section 16 of the wall 4 as a single injection molded piece of polymer material. The lower section 17 of the wall 4 advantageously comprises at its upper end 18 a socket 19 into which a lower end 20 of the upper section 16 of the wall 4 can be sealingly inserted. As also depicted in FIG. 1B (see there on the left side), at least in the region of the lower fluid space 10, a container 1 may be shaped as a PCR tube.

It is preferred that the bottom 6 of the container 1 is accomplished to form together with the wall 4 or a lower section 17 of the wall 4 a single injection molded piece of polymer material. The preferred polymer material for injection molding of the parts of the container 1 according to the invention is polypropylene. Alternately, the bottom 6 of the container 1 is accomplished as a film structure 27 that is glued or welded to the wall 4 or to a lower section 17 of the wall 4 (see e.g., FIG. 1A, left side).

The bottom 6 preferably comprises a flat area 22 on its outer side, on or in which flat area 22 an information tag 23 is located (see e.g., FIG. 1B, right side). The information tag 23 advantageously is selected from a group comprising a 1-D bar code, a 2-D bar code, an RFID transponder, and a RUBEE transceiver. The principle of 1-D and 2-D barcodes is well known to those skilled in the art and is based on the optical scanning of a high-contrast identification marking. The advantage of such identification is the relatively simple physical principle; however, there must be a visual contact between the scanning device and the information tag.

RFID transponders are also known per se and operate at high frequency (HF, such as 900 MHz) or ultra-high frequency (UHF). They transmit and receive radio signals, while the newer RUBEE transceivers operate at wavelengths below 450 kHz and emit and receive signals, which are primarily based on magnetism. The passive RFID transponders may receive approximately 100 (HF) or 150-200 (UHF) messages per second. In contrast, the active RUBEE transceivers may only receive approximately 10 messages/second; visual contact is not needed in any case. The type of information tag 23 used is thus a function, inter alia, of the density of the data transfer and the presence of a visual contact. In the case of FIG. 1B, an RFID transponder or a RUBEE transceiver is situated on the vertical wall 4 of the container 1 (see left side), while a 2-D barcode is situated on the flat area 22 of the bottom 6 (see right side). Any arbitrary combination of bar codes and RFID transponder or a RUBEE transceiver are conceivable, this is especially the case when e.g., a simple 1-D bar code is used to identify a forensic sample during collection in the field and an RFID transponder or a RUBEE transceiver is utilized on the same tube during automatic extraction of the relevant biological material in a high through put workstation of a forensic laboratory.

The container 1 preferably comprises a closure 24 for the top opening 3. Advantageously depending from the site of use, this closure 24 is selected from a group, which comprises a stopper 25, a cover 26, and a film 27. As an example, a collecting set 28 is shown in FIG. 1A. This collecting set 28 has at least one collection/extraction container 1 according to the invention. This collecting set 28 comprises a collecting rack 29 having compartments 30 for receiving the containers.

Preferably, the compartments 30 of this collecting rack 29 are open on the top and bottom, so that the containers 1 are insertable from above or below into a compartment 30 and are ejectable downward or upward from this compartment. It is especially preferred that the collecting rack 29 has the dimensions of a standard microplate. Standards for the dimensions of microplates have formally been published from ANSI (American National Standards Institute). These standards define a microplate according to the Footprint Dimensions (ANSI/SBS 1-2004), the Height Dimensions (ANSI/SBS 2-2004), the Bottom Outside Flange Dimensions (ANSI/SBS 3-2004), and the Well Positions (ANSI/SBS 4-2004). However, strip racks with six or eight compartments in one row may also be chosen for collecting forensic samples.

If the collecting set 28 originally contains sample tubes, or containers 1 respectively, without individual closure, a film 27 that covers the entire collecting rack 29 on the bottom as well as on the top is preferred (see FIG. 1A, left). Thus, perfectly clean containers that are free from any contamination are provided at the site of forensic sample collection. As soon as a fresh sample 2 has been introduced into the basket 7 of a container 1, a stopper 25 may be mounted to entirely close the top opening 3 of the container 1 (see FIG. 1A, right). The stopper 25 may contain a bar code (not shown here) that identifies the individual forensic sample 2 in the container 1.

As an alternative, the collecting set 28 may originally contain sample tubes or containers 1 with individual closure 25. In this case, at least the film 27 at the top of the collecting rack 29 can be dispensed with. If also the bottom of the compartments 30 is not covered by a film 27, the bar code can be supplied on the flat area 22 of the container bottom 6 (not shown here). Eventually, no bar code at all can be used in cases, where the containers are labeled with only an RFID transponder or a RUBEE transceiver. Such intelligent labels can also contain additional data that are entered prior to or during the sample collection and all further processing and that are readable with a dedicated device.

In the laboratory, the samples can be treated in the collecting rack 29. It is however preferred, to concentrate the containers from different collecting racks 29 and to enter them into one or more extracting racks 33. Such extracting racks 33 preferably have the shape and size of a standard microplate in order to enable transportation of these extracting racks 33 by microplate robots and handling these extracting racks 33 in microplate handling stations of laboratory workstations. An extracting rack 33 and at least one container 1 inserted into a compartment 30 of this rack forms an extracting set 32.

The containers 1 having the solid forensic sample 2 provided therein may be inserted into arbitrary compartments 30 of such extracting racks 33 by a robot (not shown). In order to accomplish this, a collecting rack 29 and an extracting rack 33 are placed on top of each other such that the compartments 30 of both racks 29,33 are in register with each other. Depending now which one of the two racks is on top of the other; a robot tool is used to push the containers 1 into the compartments of the extracting rack 33 from above of from below. This action is greatly facilitated in that both types of racks 29,33 have compartments 30 that are also open on the top and the bottom, so that the containers 1 are insertable from the bottom or top into a compartment 30 and are ejectable downward or upward from this compartment 30.

Even when processing of the containers 1 is preferred to be carried out in racks 29,33, processing each container 1 individually by a robot is possible too. That is, the containers 1 not necessarily have to be racked to be processed in an automated fashion. Actually, TECAN instruments, for instance, can move individual tubes using a so-called "Pick & Place Arm". In deed, for casework samples in forensics investigations, it is preferable to treat smaller numbers (e.g., 1 to 8) of samples simultaneously rather then wait for 96 samples. Even with smaller numbers of samples, automation provides advantages such as higher reproducibility, "chain of custody", and walk away time.

As seen from the horizontal partial sections through the two racks 29, 33 in FIG. 2, the containers 1 are preferably retained in the compartments 30 of the racks 29,33 using retention means 35 (see FIG. 2B). However, the containers 1 may sit in the compartments by friction fit only (see FIG. 2A). The containers 1 preferably have an upper flange 36 and a lower thickened area 37 that advantageously have identical external diameters. This diameter is slightly larger than the distance between two parallel intermediate walls 34 of the collecting or extracting rack 29,33. Thus, the insertion of a container slightly deforms this container and the four adjacent intermediate walls 34 and the friction between the surfaces of this upper flange 36 and lower thickened area 37 and the inner surfaces of the intermediate walls 34 keeps the container inside a compartment 30.

The FIGS. 2A and 2B are horizontal partial sections through the two racks 29,33 as shown in FIG. 1. In the right compartment of FIG. 2A and in the left compartment of FIG. 1B, a container 1 is inserted which's bottom 6 (see FIG. 1A) or which's lower section 17 of the wall 4 (see FIG. 1B) are accomplished to form a fluid collecting area 21, which is at a lower level then the rest of the bottom 6 of the container 1. This fluid collecting area 21 lies on the essentially vertical off-center axis 40. Whereas the relative position of the two other containers with respect to the inserted basket 7 (see FIG. 1A, left) or with respect to the integrated basket 7 (see FIG. 1B, right) is of no concern, the relative position of the channels 11 of the two containers with fluid collecting areas 21 is important. In order to define a correct relative position of the basket 7, channel 11 and the respective collecting areas 21 in the bottom 6 of the container 1, the basket preferably is equipped with an essentially vertical orientation bar 41. The container contains in the region of the upper sample space 9 an essentially vertical orientation grove 42 that is shaped to accommodate the orientation bar 41 of the basket 7. With this design of an orientation bar and grove 41,42, the desired position of the basket 7 may be defined in its orientation around the central axis 43 of the container 1 as well as in its height, i.e., its distance from the bottom 6 of the container 1.

Departing from the embodiment of an intermediate floor 8 as shown here with square through-openings, but not departing from the spirit of the present invention, the intermediate floor can also be made permeable to liquids by through-openings that are of any other shape than square. Different material than the Polymer used for molding the basket 7 and/or the container 1 can be used for the intermediate floor 8. Such material comprises filter paper and fabrics, which comprise natural and/or synthetic fibers and/or metal wires. However, as the containers 1 as well as the baskets 7 preferably are designed as low-cost consumables, the utilization of only one material for the production of the whole container and basket is particularly preferred.

The desired position of the basket 7 with respect to its distance from the bottom 6 of the container 1 can also be defined in that a shoulder 44 is implemented to the inner surface of the wall 4. The inner diameter of the upper sample space 9 is larger in this case than the inner diameter of the lower fluid space 10 of the container 1, this forming the shoulder 44. Accordingly, the outer diameter of the basket 7 is larger than the inner diameter of the lower fluid space 10, the basket 7 thus resting on the shoulder 44 (see FIG. 1A, left).

FIG. 3 shows vertical partial sections through an extracting rack 33 having two different embodiments of the container 1 according to the present invention. The direction of the section and viewing is indicated in FIG. 2B with arrows. Also these containers 1 preferably have an upper flange 36 and a lower thickened area 37 with identical external diameters. This upper flange 36 and this lower thickened area 37 produce a friction lock with retention means 35, which are preferably situated in the corners of the compartments 30 and extend essentially over the entire height of the compartments 30. Thanks to this friction lock, the containers are securely retained in the compartments 30 and may not fall out spontaneously. In addition, these retention means 35 may have first and second protrusions 38,39, between which the lower thickened area 37 of the container 1 snaps upon insertion into the compartment 30, so that a specific height position of the containers 1 in the compartment 30 is predefined and the retention in this defined position is reinforced further. The friction lock with the containers 1 to be inserted may be defined by the precise dimensions of these retention means 35, but also by the extent of their flexibility.

Whereas the container 1 in the left compartment of FIG. 3 is identical with the one in the right compartment of FIG. 1B, the position and size of the socket 19 at the upper end 18 of the lower section 17 of the wall 4 are different. I.e., the sockets position is lower and the height of the socket 19 is larger. In both cases however, the intermediate floor 8 is accomplished as a lattice of webs that integrally are produced in one piece with the upper section 16 of the wall 4. The ability to deliver a sealing between the two sections of the wall 4 increases with the size of the socket 19.

The container 1 preferably comprises a closure 24 for the top opening 3. Advantageously depending from the site of use, this closure 24 is selected from a group, which comprises a stopper 25, a cover 26, and a film 27. As an example, a collecting set 28 is shown in FIG. 1A. This collecting set 28 has at least one collection/extraction container 1 according to the invention. This collecting set 28 comprises a collecting rack 29 having compartments 30 for receiving the containers.

In order to be able to automatically add a liquid to the solid sample, a pipetting needle 12 can be introduced into the liquid space 10 via the channel 11 (see FIG. 1B, left) or a dispenser needle can be positioned above the solid forensic sample 2 (see FIG. 3). Also in order to automatically withdraw a liquid from the liquid space 10, a pipetting needle 12 can be introduced via the channel 11 (see FIG. 1B, left). In all cases, access through the top opening 3 of the container 1 is necessary. The top opening 3 may be entirely closed by a stopper 25 that had been mounted after collecting the forensic sample (see FIG. 1B, right) or that was put onto the container in-between two preparation steps in the lab workstation. Alternately, the top opening 3 may by partly closed by a cover 26 that covers only the sample space 9 and that leaves the channel 11 open (see FIGS. 1B and 2B, left). If the container 1 contains in the region of the upper sample space 9 an essentially vertical orientation grove 42 that is shaped to accommodate the orientation bar 41 of the basket 7, the cover 26 preferably also comprises such an orientation bar 41 (see FIG. 2B, left).

All stoppers 25 and covers 26 preferably are equipped on their top with a grasping tube 31 (see e.g., FIG. 1B), which can be grasped by a robot (not shown) in order to remove the stoppers 25 or covers 26 or in order to mount them appropriately in the containers 1. Departing from the embodiment shown but not from the spirit of the present invention, some sort of tab (e.g., like on the cover of an "Eppendorf" tube, not shown) that enables a person to easily open or remove a stopper 25 or cover 26 can be utilized as an alternate solution. A user can then open the containers 1 manually before placing them on the automation system. Again, another embodiment may include a stopper 25 or cover 26 with a pierceable septum above the basket 7 and/or channel 11 so that once the sample is placed in the basket, the stopper 25 or cover 26 does not need to be removed and the sample space 9 and/or the channel 11 can be accessed by piercing the septum on the stopper 25 or cover 26 (not shown).

The present invention also provides a method for extracting biological material from solid forensic samples 2, the method according to the invention comprises:
(a) Providing at least one container 1 with an accessible top opening 3, an upper sample space 9 with a basket 7, a fluid space 10, and a channel 11, according to the invention;
(b) Placing solid forensic samples 2, typically a swab head, cloth, WHATMAN FTA paper, or other material, containing nucleic acids through the top opening 3 into the basket 7 in the upper sample space 9 of the at least one container 1;
(c) Adding enough digestion/lysis buffer {typically a Proteinase K solution; Commercial examples include PROMEGA DNA IQ Lysis Buffer, QIAGEN Proteinase K (QIAGEN AG, Garstligweg 8, CH-8634 Hombrechtikon, Switzerland) and INVITROGEN ChargeSwitch® Lysis Buffer L13 (Invitrogen Corp., 1600 Faraday Avenue, Carlsbad, Calif. 92008, USA)} into the basket 7 so that both the lower fluid space 10 of the container 1 is filled and the upper sample space 9 is also filled enough to cover the forensic sample 2.

The actual volumes will depend on the size of the device—one imagines different size devices for different sizes of solid forensics samples 2. In one embodiment, the container 1 would be of similar dimensions to a typical 2 ml microcentrifuge tube with a basket that would likely contain a volume of about 1.25 ml. Such an embodiment would likely require adding about 1 to 1.25 ml of buffer in this step.
(d) Sealing the entire device with a film seal 27, closure 24, stopper 25, or other means and then allowing to incubate to enable the extraction process to occur. One would use the incubation times and temperatures recommended by the manufacturer of the lysis buffer (temperatures of 56° C., 70° C., and 95° C. are often used for times ranging up to an hour or more).
(e) Unsealing or opening the device 1 after incubation and removing a volume of digestion buffer by accessing the bottom of the lower fluid space 10 through the essentially vertical channel 11. The volume removed can be the entire recoverable volume but must be no less then the volume contained in both the upper sample space 9 plus the amount of liquid absorbed by the solid forensic sample 2. This recovered volume of buffer should be set aside in another vial/tube/etc of the user's choice for later processing.
(f) Placing the device 1 in a centrifuge and spinning so that any remaining buffer in the solid forensic sample collects down in the bottom of the inner chamber 5, preferably in a fluid collecting area 21. The centrifuge should be set at a speed and time that maximizes recovery of the fluid from the solid forensic sample.
(g) Removing the remaining volume of digestion buffer that has collected at the bottom of the lower fluid space 10 by the centrifugation, preferably in a fluid collecting area 21, by access through the essentially vertical channel 11. The volume removed is combined with the volume removed earlier. This sample is now ready for purification of nucleic acids using commercial nucleic acid purification kits available from companies such as PROMEGA, INVITROGEN, QIAGEN, and others.

In this device 1, volumes of lysis buffer containing nucleic acids "washed" off the solid forensic sample 2 are recovered through the "access channel" 11 so that the liquid can be removed and the solid sample 2 left behind. Thus, according to the invention, withdrawal of the lysis buffer can be carried out by a pipetting needle without requiring any removal of the basket 7 that contains the solid forensic sample. This particular feature greatly facilitates the utilization of the containers 1 in a fully automated workstation such as a TECAN style workstation that contains a device for sealing/unsealing and centrifugation (typical options on these instruments).

Using the containers according to invention, it is optional to either:
A Withdraw the extraction liquids and the extracted biological material with a pipetting needle 12 that is inserted into the channel 11 and that reaches through the sample space 9 into the fluid space 10 and to perform amplification and/or analysis of the extracted biological material outside of the container 1, or to
B Perform amplification of the extracted biological material in the fluid space 10 of the container 1.

In any case however, an incubation step preferably is carried out during the step (d) and the container 1 is centrifuged after carrying out one of the step (e).

The biological material to be extracted from the solid forensic sample can be any sort of biological material. However it is preferred to select this biological material from a group comprising bodily fluids, cells, DNA, RNA, proteins, microorganisms, and viruses. Particularly preferred is biological material in the form of nucleic acids or nucleotides.

In order to enable a workstation to carry out the method according to the invention, such a workstation preferably is equipped with robots and corresponding control systems as it is known per se in the art of liquid handling e.g., in pharmaceutical research, where chemical or biochemical compounds and/or substances are routinely assayed in regard to potential pharmaceutical effect.

In such known automatic systems, the transfer and manipulation of samples are performed by means of "workstations", as they are called, or special apparatus. These workstations may be operated individually by hand or connected together into an automated system. With automatic systems, the user does not have to carry out or provide for all the individual methods of processing. Another common factor uniting such known systems lies in the fact that samples are often processed in standardized microplates. Such microplates can be obtained in every possible format, but typically comprise 96 sample containers or "wells" arranged in a regular 8×12 raster with an interval of 9 mm between centers (according to the ANSI standards). Microplates with a multiple, or even only a part, of this number of wells are also used. Different workstations may be connected to one or more robots to carry the microplates. One or more robots, preferably moving in accordance with the system of Cartesian coordinates, may be used on a workbench top. These robots can carry plates or other sample containers and also transfer fluids. A central control system or computer monitors and controls these known systems, the outstanding advantage of which lies in the complete automation of work processes. As a consequence, such systems can be operated for hours or days on end, without the need for any human intervention.

Racks for taking up containers 1 in an array preferably have the dimensions of a standard microplate, so that the racks may be automatically grasped, transported, and placed in a microplate store or a microplate processing station, for example, using a microplate handling robot. A handling system for providing sample aliquots in racks having microplate dimensions is known from the patent EP 0 904 841 B1. The racks used therein have a peripheral frame and a top side and a bottom side. These racks comprise latticed partition or intermediate walls, which define multiple depressions or cavities, each of which is capable of receiving a sample tube or container. Special retention means prevent the sample tubes from falling out of their cavities, from which they may be removed upward or downward and may also be inserted from the top or bottom.

Any combinations of the features of the individual embodiments disclosed herein belong to the scope of the present invention. The same reference numbers are given to the same features shown in the drawings, even when they are not specifically addressed in the specification in each case.

LIST OF REFERENCE NUMERALS 1 collection/extraction container 23 information tag
2 solid forensic sample 24 closure
3 top opening 25 stopper
4 essentially vertical wall 26 cover
5 inner chamber 27 film, film structure
6 bottom 28 collecting set
7 basket 29 collecting rack
8 intermediate floor 30 compartments
9 upper sample space 31 grasping tube
10 lower fluid space 32 extracting set
11 essentially vertical channel 33 extracting rack
12 pipetting needle 34 intermediate wall
13 top orifice 35 retention means
14 bottom orifice 36 upper flange
15 partition wall 37 lower thickened area
16 upper section of the wall 38 first protrusion
17 lower section of the wall 39 second protrusion
18 upper end of lower section 40 off-center axis
19 socket 41 orientation bar
20 lower end of upper section 42 orientation grove
21 fluid collecting area 43 central axis
22 flat area 44 shoulder

The invention claimed is:

1. A collection/extraction container for a solid forensic sample, the collection/extraction container comprising:
an essentially vertical wall which encloses an inner chamber and which surrounds a top opening for the insertion of a solid forensic sample;
a bottom, which limits the inner chamber in depth, wherein the bottom and the essentially vertical wall are impermeable to fluids;
an essentially horizontal intermediate floor, which is permeable to fluids and which divides the inner chamber into an upper sample space and a lower fluid space;
an essentially vertical access channel with an essentially vertical axis, the vertical access channel being accomplished to allow a pipetting needle to be inserted through the top opening of the collection/extraction container and through the upper sample space into the fluid space, and the vertical access channel being arranged off-center with respect to a central axis of the collection/extraction container; and
a basket for the retention of the solid forensic sample in the upper sample space, the basket being formed by a side wall and the intermediate floor;
wherein the essentially vertical access channel is formed by a partition wall and the essentially vertical wall, the partition wall being in a cross-section of the container of a concave form at the access channel and thus at least partially surrounding the access channel, thereby separating the access channel from the upper sample space;
wherein the side wall of the basket is formed by the partition wall which at least partially surrounds the access channel and the basket—in its majority—is concentric to and in close contact with or formed by a part of the essentially vertical wall, so that the access channel takes a minimum space of the sample space for allowing a pipetting needle to be inserted through said sample space into the fluid space while leaving as much space as possible for a solid sample that can be introduced into the upper sample space and can be kept here by the basket; and
wherein the bottom and/or a lower section of the essentially vertical wall are accomplished to form a fluid collecting area, which is at a lower level than the rest of the bottom of the container, the fluid collecting area lying on an essentially vertical axis that is defined by the essentially vertical access channel of the container.

2. The container of claim 1, characterized in that the wall of the container is essentially cylindrical.

3. The container of claim 1, characterized in that the basket of the container is sized to accommodate a buccal swab.

4. The container of claim 1, characterized in that the basket is accomplished as a single injection molded piece of polymer material and is inserted into the inner chamber of the container.

5. The container of claim 1, characterized in that the basket is accomplished as a part of an upper section of the wall and formed together with this upper section of the wall as a single injection molded piece of polymer material.

6. The container of claim 1, characterized in that the bottom of the container is accomplished to form together with the wall or a lower section of the wall a single injection molded piece of polymer material.

7. The container of claim 6, characterized in that the lower section of the wall comprises at its upper end a socket into which a lower end of the upper section of the wall can be sealingly inserted.

8. The container of claim 1, characterized in that the bottom of the container is accomplished as a film structure that is glued or welded to the wall or to a lower section of the wall.

9. The container of claim 1, characterized in that the bottom comprises a flat area on its outer side, on or in which flat area (22) an information tag (23) is located, wherein the information tag is selected from a group comprising a 1-D bar code, a 2-D bar code, an RFID transponder, and a RUBEE transceiver.

10. The container a of claim 1, characterized in that the forensic sample is selected from a group, which comprises a gauze pad or buccal swab, a finding, a filter paper or WHATMAN FTA paper, and a textile piece.

11. The container of claim 1, characterized in that it comprises a closure for the top opening which is selected from a group, which comprises a stopper, a cover, and a film.

12. A collecting set having at least one collection/extraction container of claim 1, characterized in that the collecting set comprises a collecting rack having compartments for receiving containers.

13. The collecting set of claim 12, characterized in that the compartments of this collecting or extracting rack are open on the top and bottom, so that the containers are insertable from above or below into a compartment and are ejectable downward or upward from this compartment.

14. The collecting set of claim 12, characterized in that the collecting rack has the dimensions of a standard microplate.

15. An extracting set having at least one collection/extraction container of claim 1, characterized in that the extracting set comprises an extracting rack having compartments for receiving containers.

16. The container of claim 1, wherein the concave partition wall is providing the access channel with a lenticular cross section.

* * * * *